(12) United States Patent
Shimp

(10) Patent No.: US 6,846,853 B2
(45) Date of Patent: Jan. 25, 2005

(54) CALCIUM PHOSPHATE BONE GRAFT MATERIAL, PROCESS FOR MAKING SAME AND OSTEOIMPLANT FABRICATED FROM SAME

(75) Inventor: Lawrence A. Shimp, Morganville, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 10/196,546

(22) Filed: Jul. 16, 2002

(65) Prior Publication Data

US 2002/0183417 A1 Dec. 5, 2002

Related U.S. Application Data

(63) Continuation of application No. 09/737,369, filed on Dec. 15, 2000, now abandoned.
(60) Provisional application No. 60/173,252, filed on Dec. 28, 1999.

(51) Int. Cl.[7] .............................. A61F 2/28; C08K 3/31; A61L 27/00; B05D 3/04
(52) U.S. Cl. ....................... 523/113; 523/105; 524/117; 524/127; 524/423; 524/425; 427/2.26; 424/422; 424/426; 623/16.11
(58) Field of Search ................................. 523/105, 113; 524/117, 423, 425; 427/2.26; 424/422, 426; 623/16.11

(56) References Cited

U.S. PATENT DOCUMENTS

| 4,472,840 | A | * | 9/1984 | Jefferies | 128/898 |
| 5,683,461 | A | * | 11/1997 | Lee et al. | 424/423 |
| 5,934,287 | A | * | 8/1999 | Hayashi et al. | 128/898 |
| 5,958,504 | A | * | 9/1999 | Lee et al. | 427/2.24 |
| 6,117,456 | A | * | 9/2000 | Lee et al. | 424/602 |

OTHER PUBLICATIONS

Zyman et al, "Amorphous phase and morphological structure of hydroyapatite plasma coatings", Biomaterials, vol. 14, No. 3, pp. 225–228, 1993.*

* cited by examiner

Primary Examiner—Tae H. Yoon
(74) Attorney, Agent, or Firm—Young & Thompson

(57) ABSTRACT

A calcium phosphate bone graft material comprising an amorphous calcium phosphate glassy phase of from about 30 to about 100 volume % is obtained by plasma spraying calcium phosphate-containing powder onto a target to produce a deposited layer and removing the deposited layer from the target to provide the calcium phosphate bone graft material.

16 Claims, No Drawings

CALCIUM PHOSPHATE BONE GRAFT MATERIAL, PROCESS FOR MAKING SAME AND OSTEOIMPLANT FABRICATED FROM SAME

CROSS-REFERENCE TO RELATED APPLICATIONS

This application is a continuation of U.S. application Ser. No. 09/737,369 filed Dec. 15, 2000 which now abandoned, in turn, claims priority from U.S. Provisional application No. 60/173,252 filed Dec. 28, 1999.

BACKGROUND OF THE INVENTION

1. Field of the Disclosure

This invention relates to a calcium phosphate bone graft material, to a process for making the calcium phosphate bone graft material, and to an osteoimplant fabricated from the calcium phosphate bone graft material. More particularly, this invention relates to a calcium phosphate bone graft material composed of plasma sprayed calcium phosphate wherein the relative amounts of amorphous (glassy) phase and crystalline (ceramic) phase varies from about 100 volume % amorphous, 0 volume % crystalline to about 30 volume % amorphous, 70 volume % crystalline.

2. Description of the Related Art

An ideal artificial bone graft possesses an osteoconductive surface that bonds to bone, and dissolves (resorbs) at about the rate of bone growth so that the formation of new bone is not inhibited. Existing artificial bone grafting materials are usually quite osteoconductive, but most resorb either too quickly or too slowly.

The most commonly employed artificial grafting materials are ceramic forms of hydroxylapatite (HA), or of hydroxylapatite/tricalcium phosphate (TCP) mixtures. These ceramic materials are obtained by sintering HA or HA/TCP. Sintering is a heating process whereby crystals grow larger and more perfect to the limit where all crystals completely surround other crystals and all porosity is eliminated. The ceramic structure is therefore characterized by well-defined crystals held together by grain boundaries where different crystals touch. The more perfect the sintering conditions are, the more perfectly formed the crystals are, and the more crystalline the material is. Conventionally employed HA or HA/TCP artificial bone grafting materials contain a minimum of 80 volume % crystallinity with amounts of up to 100 volume % not being uncommon.

These highly crystalline calcium phosphate ceramics are reasonably osteoconductive (i.e., they bond to and support the growth of bone), but they resorb much more slowly than the rate of bone growth since more energy is required to disrupt a perfect crystal than a disordered structure. One approach to improving the resorbability of calcium phosphate grafting materials is to partially sinter the ceramic so that the crystals are less perfect. However, there are limits to this approach because strength decreases as the amount of sintering is decreased.

In another approach to make the ceramic calcium phosphates more resorbable, the calcium to phosphorous ratio is lowered from the 1.67 of HA to the 1.5 of TCP (or somewhere in between for mixtures of the two), to take advantage of the slightly greater solubility of TCP. TCP is more soluble than HA because only HA is stable in the presence of water (TCP is metastable). Thus, there is a driving force for TCP to dissolve since it is not stable in water. Once dissolved, it can remain in solution (if conditions are favorable), or it can later precipitate as HA by picking up additional calcium from the solution. The disadvantage to this approach is that bone is essentially HA, and TCP does not have as good bone bonding properties as HA. Other artificial bone graft materials that are not calcium phosphate ceramics include calcium sulfate, calcium carbonate, and bioglasses. Compared to the ceramics, these materials resorb much faster (sometimes faster than the rate of bone growth) and sometimes exhibit better bone bonding ability (especially the bioglasses). Bioglasses are based on short chains of silicon dioxide with added calcium and phosphate. Upon exposure to water, the calcium and phosphate reprecipitate on the surface, forming a biological HA type material. Bone bonding is excellent due to the biological apatite surface, and resorption is at about the rate of bone growth, or faster (depending on the application). Also known are glassy forms of calcium phosphates made by melting the phosphates in the presence of metals such as iron, lithium, extra calcium, etc. These glassy forms of calcium phosphates exhibit many of the properties of bioglasses, but usually have even faster resorption rates. These materials are essentially 100% glassy.

What can learned from the above is that calcium phosphate glasses possess good bone grafting properties, so long as the resorption rate is not too fast. A glass is a much more disordered structure than a ceramic or crystal, and, like all non-HA forms of calcium phosphate, is not stable in the presence of water. These properties mean that calcium phosphate glasses possess significantly higher dissolution rates than calcium phosphate ceramics, and the problem is keeping the resorption rates under control.

The bone bonding of calcium phosphate glasses is good because the relatively high solubility of the calcium and phosphate encourages the dissolution of material from the glass surface followed by reprecipitation as "bone" apatite on the surface. Bone apatite is an impure form of HA that incorporates many additional materials from surrounding body fluids such as carbonate (substituting for OH groups and/or phosphate groups), and metals such as manganese that can replace calcium.

To date, the most widely accepted way of obtaining a calcium phosphate glassy material for bone grafting is to produce a bioglass which, as mentioned above, has a silica base. A glass is made by heating a material until it melts, then cooling it in such a way that the melted, disordered structure is largely preserved. This is a slow process requiring hours or days of heating, followed by slow or fast cooling.

For many years ceramic powders made of HA (and HA/TCP or TCP) have been plasma sprayed on to orthopedic or dental implants to form osteoconductive coatings, thereby improving the integration of the implants into bone. The ceramic powder is injected into a plasma flame at temperatures of 10 to 15 times the decomposition temperatures of the ceramic, but remains in the plasma flame for only a few milliseconds while it travels to the surface of the object to be coated, where the powder immediately cools as it gives its heat up to the much larger object. When calcium phosphate ceramic powders are plasma sprayed on to implants, a two-phase coating is formed, consisting of a melted phase and an unmelted phase comprising unmelted particle cores. The melted phase yields no X-ray diffraction (XRD) pattern and therefore is non-crystalline. The unmelted particle core yields an XRD pattern that is little changed from that of the ceramic powder. The preservation of the initial ceramic powder is, in part, a consequence of the extreme rapidity of the plasma spray process.

The generally accepted theory behind plasma sprayed coatings is that the crystalline, ceramic phase is the functional part of the plasma sprayed calcium phosphate coating. Bone bonds to this crystalline phase in the coating the same as it bonds to solid, ceramic implants. However, the opposite is actually true. The amorphous, non-crystalline phase is responsible for the excellent biological properties of calcium phosphate coatings. Plasma sprayed coatings exhibit a better bone response than the corresponding non-plasma sprayed solid calcium phosphate ceramics, and also resorb at a faster rate. In their osteoconductive and resorption properties, plasma sprayed coatings can be considered to be between calcium phosphate ceramics and bioglasses.

The amorphous phase is a type of calcium phosphate glass formed by extremely rapid melting and extremely rapid cooling. Glassy materials can be produced by any method that provides very fast heating and cooling. For example, laser melting can be adapted to this process, as well as all forms of plasma spraying including flame spraying, vacuum plasma spraying, high velocity oxygen fuel (HVOF) spraying, etc. For purposes of this invention, plasma spraying shall be understood as being inclusive of all methods that provide very fast heating and cooling.

The improved biological response of plasma sprayed HA or other calcium phosphates compared to ceramic forms render them desirable as bone grafting materials. However, plasma sprayed calcium phosphates are currently only available as coatings, and not as grafting materials in their own right.

SUMMARY OF THE INVENTION

A calcium phosphate bone graft material is provided which comprises amorphous calcium phosphate obtained by plasma spraying a calcium phosphate-containing powder onto a target to provide a plasma-sprayed calcium phosphate layer thereon and removing the layer from the target to provide the calcium phosphate bone graft material. The removed material can be further treated to produce granules ranging in size from about 50 to about 4000 microns. The amorphous (glassy) phase of the bone graft material of this invention ranges from about 30 to about 100 volume percent of the material, with the remainder (if any) being made up of crystalline (ceramic) phase. In a variation on the process, the target can contain cavities that become filled with the plasma sprayed calcium phosphate-containing powder of such size and configuration that removal of the material from the target results in preformed articles of the size and configuration of the cavities.

The bone graft material can be fabricated into an osteoimplant by a variety of different methods. In accordance with one embodiment, the material is removed from the target, ground and sieved to produce a granulate which is then admixed with a suitable biocompatible fluid, e.g., water, saline, dilute phosphoric acid, to form a slurry or paste which can be applied to the bone healing site. In another embodiment, the bone graft material can be placed in a mold and compressed under suitable pressure, optionally in the presence of elevated temperature ranging from about 50° C. to as high as about 500° C. (if pressing is conducted in a closed vessel such as is employed in hot isostatic pressing), to form a solid aggregate capable of initially bearing loads in vivo. Alternatively, the granulate can be combined with a binder material and compressed to form the solid aggregate. In accordance with another embodiment, the granules are admixed with bone-derived elements, such as bone particles that have been optionally demineralized, to form an osteoconductive implant. In accordance with another embodiment, the granules are blended with a suitable biocompatible polymer such as polyglycolic acid, polyglycolide, polylactic acid, polylactide, and the like, to form an osteoconductive implant.

DESCRIPTION OF THE PREFERRED EMBODIMENTS

It is preferred to start with a ceramic powder as the material to be plasma sprayed because the strength and stability of the powder particles towards moisture pick up makes the material easier to handle. However, it is possible to use unsintered powder as well. The source of the powder for spraying can be made by a variety of processes such as precipitation, solid liquid reactions (such as is used to make calcium phosphate cements), bovine bone particles, etc.

The calcium phosphate-containing powder utilized in accordance with the practice of the present invention will generally contain hydroxylapatite in an amount of at least about 60 weight percent, with the balance (if any) being composed of one or more materials selected from the group consisting of tricalcium phosphate, dicalcium phosphate, tetracalcium phosphate, calcium oxide, calcium hydroxide, calcium carbonate, soluble crystalline phases, and traces of glass promoting elements such as iron. The starting material is preferably HA in order to retain the Ca/P ratio of HA in the glass. This helps to enable a faster transformation of the glass to a biological apatite once it is implanted, and so enhances osteoconductivity. However, other calcium phosphates, or mixtures, can also be made into glassy particles by the same means and used for bone grafting applications. Varying the Ca/P ratio is a way of "tuning" the bone bonding and resorption properties.

In accordance with one embodiment, the calcium-phosphate-containing powder comprises animal (including human) bone tissue that is ground to a powder of a suitable size for plasma spraying. Before spraying the powder can be treated by heating it to a temperature of up to about 500° C. to burn out the organic matter and, optionally, further heating the powder to a temperature of up to about 1100° C. to sinter the powder.

The calcium phosphate-containing powder is plasma sprayed onto a target in accordance with conventional techniques to provide a layer thereon ranging in thickness from about 0.5 to about 100, preferably from about 10 to about 30, mm.

The method of applying the calcium phosphate-containing powder to the target employs a plasma spray system or plasma detonation system. Plasma spray systems are manufactured and marketed under the tradename Metco 7M and Metco 9M 80 kW spray systems. Plasma detonation systems are manufactured and marketed under the trade name Metco Diamond Jet Gun System. The plasma spray system and the plasma detonation system are available from the Metco Division of Sulzer. A second source of equipment suitable for use with the present invention is Miller Thermal based in Appleton, Wis.

A Metco control unit FMCII and Metco AR2000 6 degree of freedom robot system may be employed to aid in applying the calcium phosphate-containing powder. A Metco 4MP feeder may be employed to deliver the powder to the plasma gun. The foregoing equipment is also available from Sulzer.

Plasma spray systems operate by injecting a ceramic powder to the inert gas plasma generated by the plasma gun. The plasma gun accelerates the ceramic particles to a very high velocity at a very high temperature. The high velocity high temperature plasma spray is directed toward the target where the particles of the ceramic material strike and coat the target to impregnate (penetrate) the target to form an adherent coating. The adherent coating extends into the preexisting surface pores of the target due to the high velocity of the ceramic material. The plasma spray may be allowed to build up past the surface of the target.

A carrier gas, which is preferably argon or nitrogen, is required to carry the ceramic powder into the electric arc of the plasma gun. The particles of the ceramic material are entrained in a jet of the carrier gas which passes through the electric arc. The power to the electric arc allows differing ceramic particle sizes to be used. The gun may also be varied to provide that the ceramic material strikes the target at a velocity sufficient to cause adherence to the target.

When desired a plasma detonation system may be employed to deliver to the ceramic material to the target. The process in a plasma detonation system is generally similar to the conventional plasma spray process described above. The plasma detonation gun system differs in detonating a mixture of hydrogen and oxygen near the tip of the nozzle through which the ceramic material is fed. The detonation of hydrogen and oxygen in the plasma detonation gun system significantly increases the velocity of the ceramic particles in the plasma.

Thereafter, the plasma sprayed layer is removed from the target, e.g., by scraping the surface of the target, to recover the calcium phosphate bone graft material of this invention. The material can be advantageously treated, e.g., by grinding and sieving the material, to produce particle sizes within a desired range. The average particle sizes of the treated material will generally range from about 50 to about 4000, preferably from about 100 to about 1000, microns.

By varying the plasma spraying conditions, the relative amounts of crystalline (ceramic) phase and glassy phase in the material can be varied from about 100 volume % glassy, 0 volume % crystalline to 30 volume % glassy, 70 volume % crystalline. The relative amounts of glassy and crystalline material can influence both the bone binding properties and the rate of resorption, and so provide another way of fine tuning the properties in addition to varying the calcium to phosphorus ratio.

The following examples illustrate the practice of the present invention.

EXAMPLE 1

Sintered HA powder, with a crystallinity of nearly 100% and a particle size of 90% between 1 and 40 microns was sprayed with a METCO 9MB plasma gun, running on nitrogen, at 350 amps and 60 volts, at a feed rate of 16 grams/minutes on to a stainless steel target 70 mm from the gun. The gun was traversed by a robot in steps of 3 mm each, at a speed of 200 mm/minute. The coating was build up with 20 passes to a thickness of 5 mm. It was then removed from the target, crushed in a mortar, and sieved through a 125 micron screen and collected on a 75 micron screen. The resulting granulate was analyzed by X-ray diffraction and found to have a crystallinity of 35 volume %. The glassy phase represented 65 volume % of the material.

EXAMPLE 2

The material described in Example 1 was implanted in femoral defects created in rats. As a control, defects were filled with ceramic HA particles (98 to 99% dense, 100% crystalline, 75 to 125 microns in diameter). Fifteen male Long Evans rats from Harlan Sprague Dawley, Inc. (Indianapolis, Ind.) were implanted with the materials. The animals were 300 g or greater at the time of surgery. The right thigh muscle of the rat was separated to expose the full-length of the femur. A polyethylene plate was placed along the length of the femur and anchored with four pins. A 5 mm section of the femur was removed between pins 2 and 3 to create a 5 mm critical defect (a defect so large that the bone will not heal by itself). The defect was filled with 300 mg of the amorphous material from Example 1, or 300 mg of the control ceramic HA particles. Both materials were soaked in approximately 100 ul of sterile saline/blood mixture prior to implantation. No complications occurred during surgery, however two animals died immediately post surgery, and three animals were later euthanized for fractures. The femurs from the remaining ten animals were retrieved after an implantation time of 84 days. There were five femurs for each of the two implant materials. Histological analysis showed only fibrous tissue contact with the ceramic HA particles; that is, there was no direct bone contact with any of the ceramic HA particles. In contrast, for the amorphous particles, bone contacted and fully surrounded the amorphous particles at the outer layer of the graft site and partially surrounded some particles up to 1 mm in towards the center of the graft site. This demonstrates the much more favorable properties of the amorphous material as a scaffold for bone growth compared to the ceramic HA particles.

What is claimed is:

1. A calcium phosphate bone graft material, comprising:
an amorphous calcium phosphate glassy phase representing from about 30 to about 100 volume % of the total volume of the calcium phosphate bone graft material,
said graft material being obtained by plasma spraying calcium phosphate-containing powder onto a target to produce a deposited layer thereon and removing the deposited layer from the target to provide the calcium phosphate bone graft material.

2. The bone graft material of claim 1 possessing an average particle size of from about 50 to about 4000 microns.

3. An osteoimplant comprising the calcium phosphate bone graft material of claim 1.

4. The osteoimplant of claim 3 further comprising at least one bone-derived element.

5. The osteoimplant of claim 4 wherein the bone-derived element comprises demineralized bone particles.

6. The osteoimplant of claim 3 further comprising at least one biocompatible polymer.

7. A method of making a calcium phosphate bone graft material which comprises the steps of:
providing a calcium phosphate-containing powder;
plasma spraying the calcium phosphate-containing powder onto a target to provide a deposited layer thereon; and
removing the deposited layer to provide a calcium phosphate bone graft material wherein the amorphous glassy phase represents from about 30 to about 100 volume % of the total volume of the calcium phosphate bone graft material.

8. The method of claim 7 wherein the target contains cavities.

9. The method of claim 7 wherein the average particle size of the calcium phosphate bone graft material is from about 50 to about 4000 microns.

10. The method of claim 7 which further comprises the step of compressing the calcium phosphate bone graft material under pressure to form a solid aggregate.

11. The method of claim 10 wherein the calcium phosphate bone graft material comprises bone-derived elements in combination therewith.

12. The method of claim 10 wherein the calcium phosphate bone graft material comprises a biocompatible polymer in combination therewith.

13. A method of treating a bone defect which comprises the steps of:

providing the calcium phosphate bone graft material of claim 1; and placing the calcium phosphate bone graft material inside the bone defect.

14. The method of claim 7 wherein the calcium phosphate-containing powder comprises sintered or unsintered hydroxyapatite, sintered or unsintered tricalcium phosphate, and mixtures thereof.

15. The method of claim 7 wherein the calcium phosphate-containing powder further comprises calcium carbonate, calcium sulfate, or mixtures thereof.

16. The method of claim 7 wherein the calcium phosphate-containing powder comprises animal bone tissue which has been heat treated to remove the organic constituents thereof.

* * * * *